United States Patent
Richards-Kortum et al.

(10) Patent No.: US 7,365,844 B2
(45) Date of Patent: Apr. 29, 2008

(54) VISION ENHANCEMENT SYSTEM FOR IMPROVED DETECTION OF EPITHELIAL NEOPLASIA AND OTHER CONDITIONS

(75) Inventors: Rebecca Richards-Kortum, Austin, TX (US); Urs Utzinger, Tucson, AZ (US); Ekaterina S. Svistun, Santa Rosa, CA (US); Ann Gillenwater, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 285 days.

(21) Appl. No.: 10/732,199

(22) Filed: Dec. 10, 2003

(65) Prior Publication Data

US 2005/0080343 A1    Apr. 14, 2005

Related U.S. Application Data

(60) Provisional application No. 60/432,122, filed on Dec. 10, 2002.

(51) Int. Cl.
    *G01J 3/28* (2006.01)
(52) U.S. Cl. .................................. 356/326; 600/476
(58) Field of Classification Search ............... 600/476; 356/326
    See application file for complete search history.

(56) References Cited

U.S. PATENT DOCUMENTS 4,321,251 A    3/1982  Mashberg ..................... 424/3
4,930,516 A *  6/1990  Alfano et al. ................ 600/477
5,507,287 A *  4/1996  Palcic et al. ................. 600/317
6,870,616 B2 * 3/2005  Jung et al. ................... 356/326

OTHER PUBLICATIONS

Jordan, III et al., "Color as a source of information in the stereo correspondence process," Vision Res., 20:1955-1970.
Jullien et al., "Evaluation of a screening test for the early detection of oral cancer and precancer," *Community Dent. Health*, 12:3-7, 1995.
Kaiser and Boynton, *Human Color Vision*, 2nd ed., Optical Society of America, 1996.
Lakowicz, *Principles of Fluorescence Spectroscopy*, 2nd Ed., New York: Plenum Press Publishers, 1999.
Lakowicz, *Principles of Fluorescence Spectroscopy*, New York: Plenum Press, 1985.
MacAdam, "Visual sensitivities to color differences in daylight," *Journal of the Optical Society of America*, 32:247-274, 1942.
Müeller et al., "Spectroscopic detection and evaluation of morphologic and biochemical changes in early human oral carcinoma," *Cancer*, 97:1681-1692, 2003.

(Continued)

*Primary Examiner*—Brian L. Casler
*Assistant Examiner*—John F. Ramirez
(74) *Attorney, Agent, or Firm*—Fulbright & Jaworski L.L.P.

(57) ABSTRACT

Systems and methods for diagnosing epithelial neoplasia and other conditions includes, in a representative embodiment, providing the human eyes with a filter to observe the autofluorescence of a tissue sample. Using optimized wavelengths from a filtered light source, a sample is illuminated. The radiation from the sample is filtered to enhance the contrast between a normal sample and a diseased sample observable by the human eye.

28 Claims, 6 Drawing Sheets

OTHER PUBLICATIONS

Onizawa et al., "Fluorescence photography as a diagnostic method for oral cancer," *Cancer Lett.*, 108:61-66, 1996.

Ramanujam, "Fluorescence spectroscopy of neoplastic and non-neoplastic tissues," *Neoplasia*, 2(1-2):89-117, 2000.

Richards-Kortum and Sevick-Muraca, "Quantitative optical sectroscopy for tissue diagnosis," *Annual Reviews in Physical Chemistry*, 47:555-606, 1996.

Richards-Kortum et al., "Cervical dysplasia diagnosis with fluorescence sepctroscopy," in: *Fluorescence in Biomedicine*, Chapter 9, Marcel Dekker, Ed., 2001.

Robertson, "The CIE 1976 color difference formulae," *Color Res. Appl.*, 2:7-11, 1977.

Schantz et al., "In vivo *native cellular fluorescence and histological characteristics of head and neck cancer*," *Clin. Cancer Res.*, 4:1177-1182, 1998.

Sokolov et al., "Realistic three-dimensional epithelial tissue phantoms for biomedical optics," *Journal of Biomedical Optics*, in press, 2001.

Stockman and Sharpe, "Spectral sensitivities of the middle- and long-wavelength sensitive cones derived from measurements in observers of known genotype," *Vision Res.*, 40:1711-1737, 2000.

Svistun et al., "Vision enhancement system for detection of oral cavity neoplasia based on autofluorescence," Head and Neck, 2003.

Trujillo et al., "A method to determine tissue fluorescence efficiency in vivo and predict signal to noise ratio for spectrometers," *Appl. Spectrosc.*, 52:943-951, 1998.

U.S. Department of Health and Human Services, Centers for Disease Control and Prevention, "Colorectal cancer: the importance of prevention and early detection," Atlanta, GA, 2001.

U.S. Department of Health and Human Services, Centers for Disease Control and Prevention, "Improving oral health: preventing unnecessary disease among all Americans," Atlanta, GA, 2001.

Utzinger et al., "Cancer screening through the use of enhanced visual systems," Proceedings of SPIE, 4259, 2001.

Utzinger et al., "Optimal visual perception and detection of oral cavity neoplasia," *IEEE Transactions on Biomedical Engineering*, 50(3):396-399, 2003.

Wagnieres et al., "In vivo fluorescence spectroscopy and imaging for oncological applications," *Photochemistry & Photobiology*, 68(5):603-632, 1998.

Wandell B., *Foundations of Vision*, Sunderland, MA: Sinauer Associations, 1995.

Wyszecki and Stiles, "The CIE colorimetric system," In: *Color Science, Concepts and Methods, Quantitative Data and Formulae*, 2nd Ed., New York: John Wiley & Sons, 1982.

Wyszecki, *Color Science, Concepts and Methods, Quantitative Data and Formulae*, 2nd Ed., New York: John Wiley & Sons, 1982.

Zuluaga et al., "Fluorescence excitation emission matrices of human tissue: a system for in vivo measurement and method of data analysis," *Applied Spectroscopy*, 53(3):302-311, 1999.

American Cancer Society, "Cancer facts & figures—2001," American Cancer Society, Atlanta, GA, 01-300M-No. 5008.01, 2001.

Andersson-Engels et al., "In vivo fluorescence imaging for tissue diagnostics," *Phys. Med. Biol.*, 42:815-824, 1997.

Benavides et al., "Multispectral digital colposcopy for in vivo detection of cervical cancer," *Optics Express*, 11(10):1223-1236, 2003.

Bergenholtz and Welander, "Ultraviolet autofluorescence: an aid in oral diagnosis," *Dent. Radiogr. Photogr.*, 43:83-89, 1970.

Bernes, *Billmeyer and Saltzman's Principles of Color Technology*, 3rd edition, New York: John Wiley and Sons, Inc., 2000.

Betz et al., "Autofluorescence imaging and spectrometry of normal and malignant muscosa in patients with head and neck cancer," *Laser Surg. Med.*, 25:323-334, 1999.

Blair and Callendar, "Head and neck cancer-the problem," *Clin. Plast. Surg.*, 21:1-7, 1994.

Boff et al., *Handbook of Perception and Human Performance*, vol. 1, Sensory Processes and Perception, John Wiley and Sons, undated.

Brookner et al., "Autofluorescence patterns in short-term cultures of normal cervical tissue," *Photochem. Photobiol.*, 71:730-736, 2000.

Commission International de L'Eclairage, "Colorimetry 2nd edition," CIE, Vienna, Austria, CIE, 15.2, 1986.

Drezek et al., "Autofluorescence microscopy of fresh cervical-tissue sections reveals alterations in tissue biochemistrty with dysplasia," *Photochem. Photobiol.*, 73:636-641, 2001.

Geisler, "Discrimination information in natural radiance spectra," In: *Vision Models for Target Detection and Recognition*, E. Peli, Ed. Singapore: World Scientific Publishing, 1995.

Geisler, "Sequential ideal-observer analysis of visual discriminations," *Psychological Review*, 96(2):267-314, 1989.

Georgakoudi et al., "Fluorescence, reflectance, and light scattering spectrometry for evaluating dysplasia in patients with Barrett's esophagus," *Gastroenterology*, 120:1620-1629, 2001.

Gillenwater et al., "Noninvasive diagnosis of oral neoplasia based on fluorescence spectroscopy and native tissue autofluorescence," *Arc.Otolaryngol. Head Neck Surgery*, 124, 1998.

Glasser and Troy, "A new high sensitivity differential colorimeter," *Journal of the Optical Society of America*, A, 42:652-660, 1952.

Glasser et al., "Cube-root color coordinate system," *Journal of the Optical Society of America*, A, 48:736-740, 1958.

Guenther and Stiles, "Color science: concepts and methods," Quantitative Data and Formulae, 2nd Ed., Wiley-Interscience Publication, no date.

Guo et al., "Allelic losses in OraTest-directed biopsies of patients with prior upper aerodigestive tract malignancy," *Clin. Cancer Res.*, 7:1963-1968, 2001.

Guth et al., "Vector model for normal and dichromatic color vision," *Journal of the Optical Society of America*, A, 70:197-212, 1980.

Guth, "Model of color vision and light adaption," *Journal of the Optical Society of America*, A, 8(6):976-993, 1991.

Harries et al., "Diagnostic imaging of the larynx: autofluorescence of laryngeal tumours using the helium-cadmium laser," *Journal of Laryngology & Otology*, 109(2):108-110, 1995.

Heintzelman et al., "Optical excitation wavelenghs for in vivo detection of oral neoplasia using fluorescence spectroscopy," *Photochemistry and Photobiology*, 72:103-113, 2000.

\* cited by examiner

VISION ENHANCEMENT SYSTEM FOR IMPROVED DETECTION OF EPITHELIAL NEOPLASIA AND OTHER CONDITIONS

This application claims priority to and incorporates by reference, U.S. Provisional Patent Application Ser. No. 60/432,122, which was filed on Dec. 10, 2002.

BACKGROUND OF THE INVENTION

1. Field of the Invention

The present invention relates generally to optics and spectroscopy. More particularly, the present invention relates to diagnosing epithelial neoplasia and other conditions using optimized spectroscopy observable by the human eye.

2. Background

Approximately 1,200,000 people were diagnosed with cancer in 1999 resulting in approximately 563,000 deaths. The majority of these cancers were of epithelial origin. Early detection of pre-invasive epithelial neoplasia has the potential to increase patient survival and improve quality of life. However, many of the currently available screening and detection techniques for epithelial pre-cancers do not provide adequate sensitivity and specificity; furthermore, many screening and detection methods require extensive training to yield adequate clinical results. For example, to discern between premalignant and early malignant lesions from common benign inflammatory in suspected oral cancer cases, practitioners commonly perform visual examinations. However, visual screenings have been reported to have a sensitivity of only 74%, a specificity of 99%, and a negative predicative value of 0.67 and 0.99, respectively. Consequently, practitioners often resort to the invasive and painful option of biopsies to confirm the presence of precancer or even early cancer. Thus, despite the easy accessibility of the oral cavity for examination, current methods do not adequately screen and detect precancers in a non-invasive manner.

There is a need for a non-invasive tool to diagnose epithelial neoplasia, such as oral cancer, skin cancer, and cervical cancer that yields accurate results.

SUMMARY OF THE INVENTION

Shortcomings of the prior art are reduced or eliminated by the techniques discussed in this disclosure. In one embodiment, the invention includes a system. The system may include a filter that filters radiation from an illumination source for one or more wavelengths between the ranges of about 300 and 625 nanometers, where the illumination source may be a white light source. The filter may also filter radiation from the illumination source to one or more wavelengths between about 400 and 590 nanometers. A ratio between two or more filtered wavelengths from the source may be optimized to increase observable contrast between a diseased sample and a normal sample to a human eye.

The system may further include a light guide that delivers the one or more wavelengths to a sample. The radiation that may be emitted from the sample may be filter by a viewing device of the system. The viewing device may include at least one long bandpass filter that filters the radiation from the sample to one or more wavelengths between about 320 and 625 nanometers to allow a human eye to differentiate between a diseased sample and a normal sample. The viewing device may be glasses that include observation filters to review the sample. The viewing device may also be a camera, where the camera may be attached to a colposcope. An attenuation ratio between two or more filtered wavelengths from the sample may be optimized to increase observable contrast between a diseased sample and a normal sample to a human eye.

The long bandpass filter may also filter radiation from the sample to one or more wavelengths between about 330 and 470 nanometers. For a sample that may include cervical cancer, the long bandpass filter may filter radiation from the sample to one or more wavelengths between about 330 to 360 and 440 to 470 nanometers to allow a human eye to discern if the sample is normal or not. In addition, for a sample that may contain oral cancer, the long bandpass filter may filter radiation from the sample to one or more wavelengths between 420 to 470 nanometers to allow a human eye to determine if the sample does include oral cancer.

In one embodiment of the invention, a system may include a filter that filters radiation from an illumination source to one ore more wavelengths ranging from about 250 and 700 nanometers. The one or more wavelengths are directed to a sample via a light guide. The radiation from the sample may be filter by at least one long bandpass filter that filters one or more wavelengths between about 320 and 700 nanometers. The one or more filtered radiation from the sample may be observed by a human eye to discern if the sample is diseased or not.

In one respect, the invention involves a method for viewing a sample. One or more wavelengths between about 300 and 625 nanometers are filtered from a illumination source and may be directed towards a sample. The radiation from the sample is filtered to one or more wavelengths between about 320 and 700 nanometers to form a filtered image. The filtered image is viewed by a human eye to discriminate between a diseased sample and a normal sample. Viewing may include glasses with observation filters that allow the human eye to see the fluorescence reflected from the sample, and thus discriminate between a normal sample and a diseased sample. Further, viewing may include a camera that captures the radiation from the sample and where the images produce from the camera may allow a human eye to discern between a normal sample and a diseased sample.

A ratio between two or more filtered wavelengths from the illumination source is optimized to increase observable contrast between a diseased and a normal sample to a human eye. Further, an attenuation ratio between two or more filtered wavelengths from the illumination source is optimized to increase observable contrast between a diseased and a normal sample to a human eye.

The diseased sample may be epithelial neoplasia including, but is not limited to skin cancer, cervical cancer, and oral cancer. Oral cancer may be defined as pharaynx neoplasia, throat neoplasia, paranasal sinus neoplasia, nasal cavity neoplasia, larynx neoplasia, thyroid neoplasia, parathyroid neoplasia and/or salivary gland neoplasia.

The method may also include filtering the radiation from the illumination source to one or more wavelengths between about 400 and 590 nanometers using a bandpass filter. The one or more wavelengths may be directed to the sample using a light guide. Radiation emitted from the sample may be filtered using a long bandpass filter that may filter for one or more wavelengths between about 330 and 470 nanometers. To discern if the sample is a diseased sample or a normal sample, the long bandpass filter may filter radiation from the sample to one or more wavelengths between about 330 to 360 and about 440 and 470 nanometers to differentiate if the sample includes cervical cancer or is a normal sample. Further, the long bandpass filter may filter radiation from a sample to one or more wavelengths between 420 and 470 nanometers to differentiate if the sample includes oral cancer or is a normal sample.

Other features and associated advantages will become apparent with reference to the following detailed description of specific embodiments in connection with the accompanying drawings.

BRIEF DESCRIPTION OF THE DRAWINGS

The techniques of this disclosure may be better understood by reference to one or more of these drawings in combination with the detailed description of illustrative embodiments presented herein. Identical reference numbers signify identical or similar elements.

DESCRIPTION OF ILLUSTRATIVE EMBODIMENTS

Noninvasive and accurate techniques that facilitate the early detection of neoplastic changes improve survival rates and lower treatment costs by reducing or eliminating other diagnostic procedures. Optical tools using knowledge of light and tissue interaction can provide fast, noninvasive methods of cancer diagnosis. Normally, reflected white light on objects is observable because of a dominant light-tissue interaction. However, it is also possible to observe tissue autofluorescence, in which optical contrast between normal and neoplastic tissue might be significantly greater. When molecules within tissue absorb incident light, they can release energy in the form of fluorescent light. The intensity and color of the fluorescence gives information about the local biochemical composition of tissue. Molecules capable of emitting light caused by optical excitation are called fluorophores. Autofluorescence originates from many endogenous fluorophores present in the tissue such as the crosslinks in the structural proteins collagen and elastin, the metabolic co-factors nicotinamide adenine dinucleotide (NADH) and flavin adenine dinucleotide (FAD+), aromatic amino acids, such as tryptophan, tyrosine, and phenylalanine, and porphyrins. Tissue fluorescence signatures are of particular interest, because spectral changes might reflect changes in metabolic activity and communication between the epithelium and the stroma.

Although visual examination remains the mainstay for diagnosis of many cancers such as skin, cervical, and oral, the human eyes are not optimized for the visual detection of neoplastic diseases. Ordinarily, tissue fluorescence is not visible by eye, because it is masked by much more intense reflected light. The human eye can only extract a fraction of the existing chromatic information because of the physiologic properties of the color detection mechanisms. The three types of cone photoreceptors have broadly overlapping spectral sensitivities, which might reduce the potential diagnostic contrast available when viewing tissue fluorescence.

As such, embodiments of the present invention provide an autofluorescence imaging system and method in which the illumination and observation conditions have been optimized to take into account the limitations of the human visual system. Representative embodiments relate to providing a viewing device, such as filter glasses or cameras that capture the images from a sample to observe tissue fluorescence with a human eye.

Figure 1:
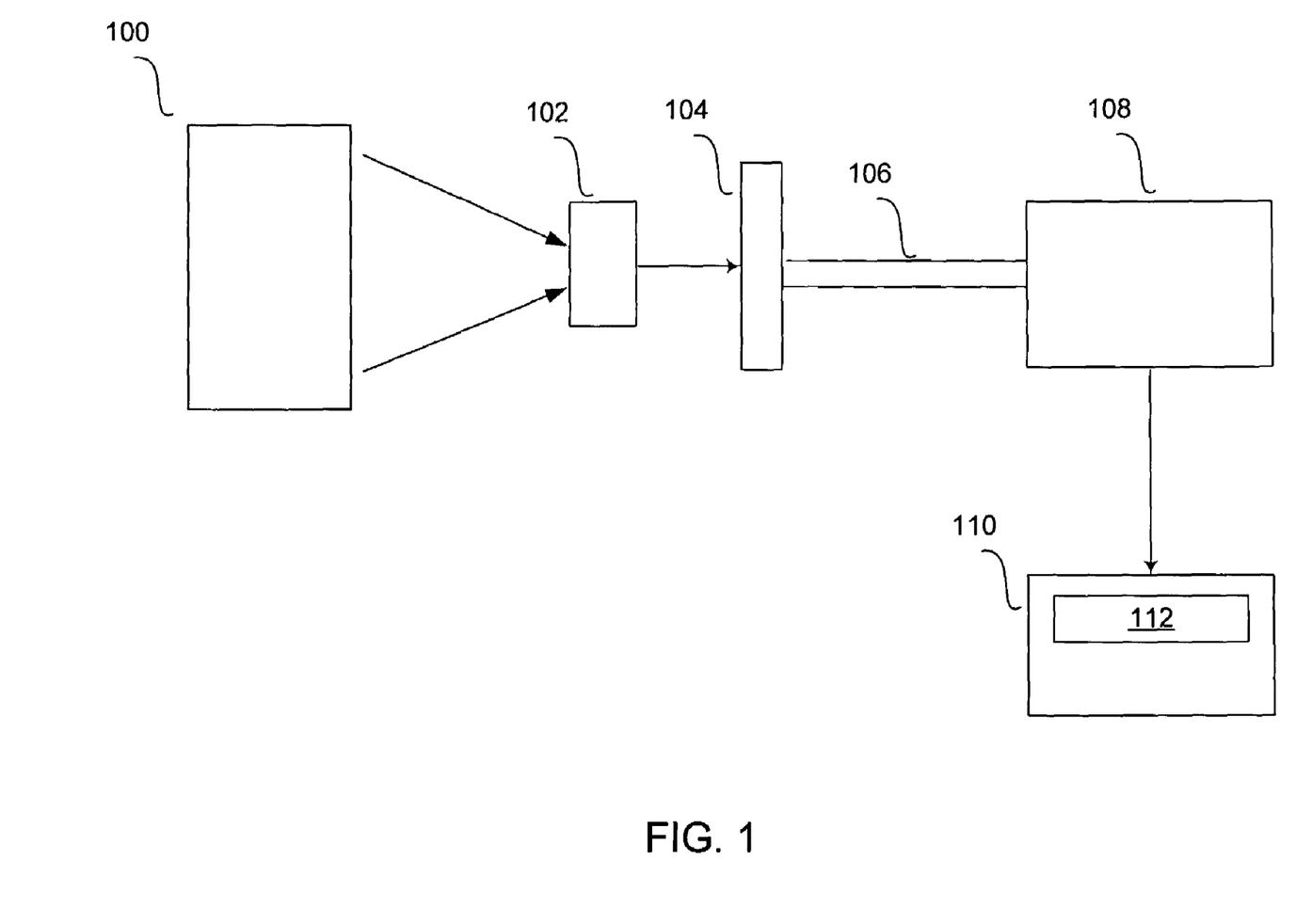
FIG. 1 is a block diagram of a system for diagnosing epithelial neoplasia.

A diagram of a system used to excite and view tissue fluorescence is illustrated in FIG. 1. The system includes light source 100. In one embodiment, light source 100 is a white light source such as a Xenon, Tungsten, or Mercury lamp. Cold mirror 102 rejects radiation from light source 100. In one embodiment, it rejects radiation below 300 nm and above 625 nm, preventing UV and infrared radiation from light source 100 from reaching the filter wheel 104. The cold mirror 102 directs an illumination beam (which can be collimated) into a filter wheel 104 which houses at least one bandpass filter. The filter wheel selects emission wavelength regions. In one embodiment, one of the filter wheel slots is left empty to provide white light illumination.

The wavelengths may pass through the filter and may be focused onto a light guide 106, such as a flexible fiberoptic bundle, which can be used as an illuminator onto a sample. In one embodiment, the bundle may be 5 mm in diameter and filled with 200-Am core diameter quartz fibers. The light guide 106 may be used to illuminate sample 108, such as an entire oral cavity or a tissue sample. In one embodiment, the optimal operating distance can be about 20 to 30 cm, illuminating a surface from about 4 to 8 cm in diameter.

The radiation, or fluorescence, from the sample 108 may be observed with a viewing device 110, such as glasses containing observation filters, such as long bandpass filter 112. In one embodiment, long bandpass filter 112 can have a maximum transmittance at 590 nm (60-nm bandwidth). Long bandpass filters may be used to suppress reflected illumination light. In another embodiment, the viewing device 110 may be a camera containing long bandpass filter 112 used to document autofluorescence.

Figure 2:
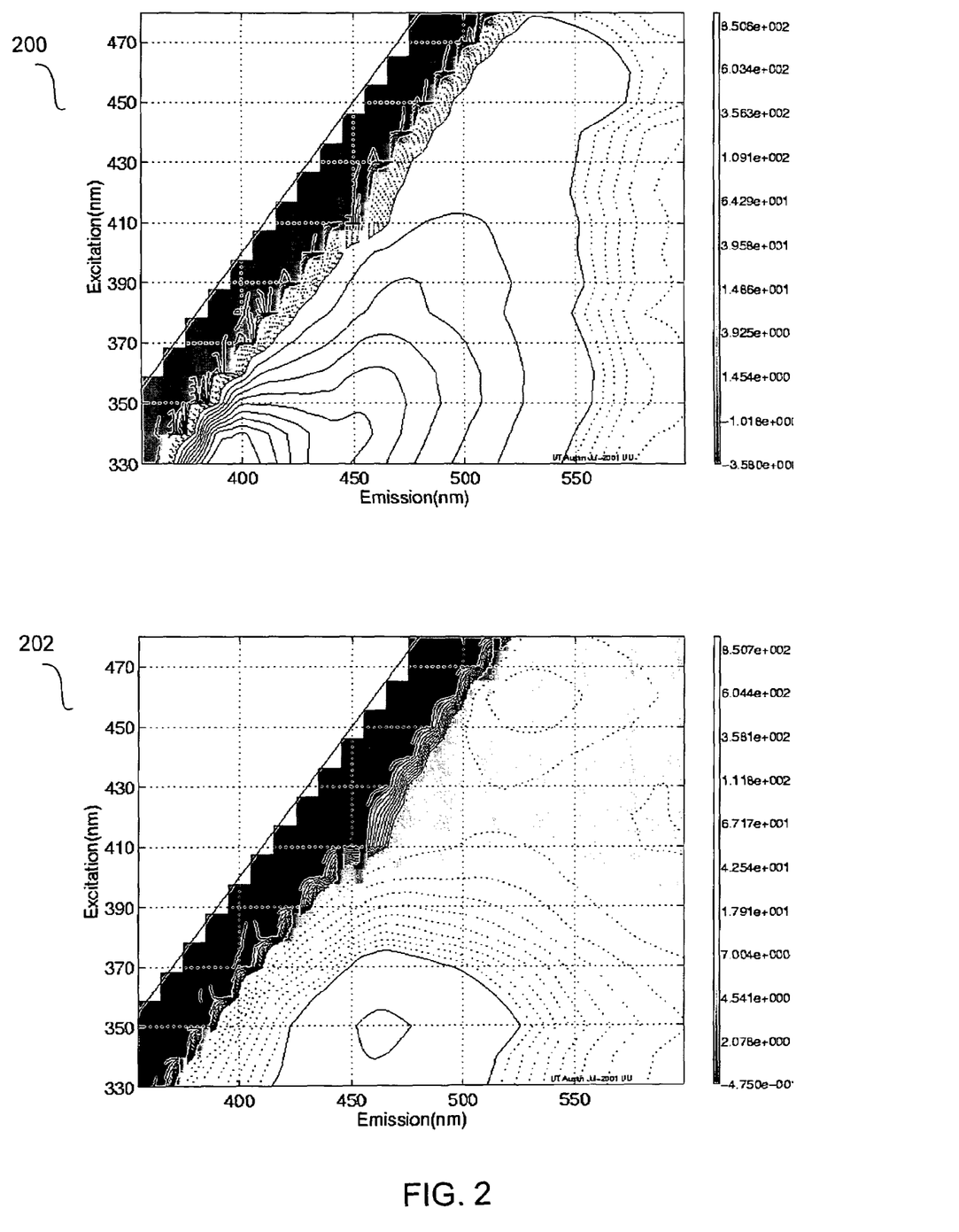
FIG. 2 are excitation emission matrices (EEM) of a normal sample and a diseased sample.

In one embodiment, the system measures emission spectra at a plurality of different excitation wavelengths, ranging from 330 to 480 nm. The radiation range from the illumination source may be limited between 400 nm to 590 nm. At 400 nm spectra can be truncated because of the human eye's lower wavelength limit, and above 590 nm spectral data can be truncated because the ratio of fluorescence to background light may be low. Example fluorescence EEMs are presented in FIG. 2. The fluorescence emission of normal site 200 shown is stronger than the cancerous site 202. The cancerous site 202, however exhibits stronger hemoglobin absorption of the fluorescence light at 420 nm excitation and emission wavelength, resulting in horizontal and vertical valleys in the fluorescence emission plot in FIG. 2.

Figure 3A:
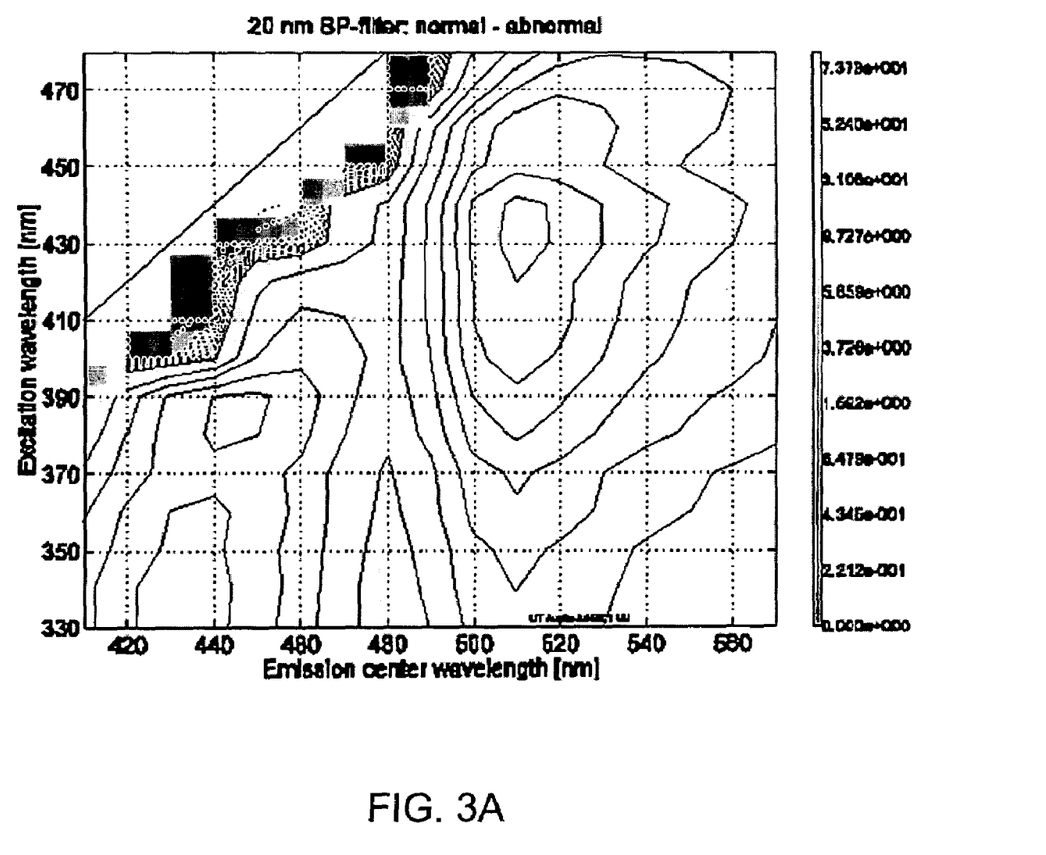
FIG. 3A is an excitation emission matrix of a sample through a bandpass filter with 20 nm bandwidth.
Figure 3B:
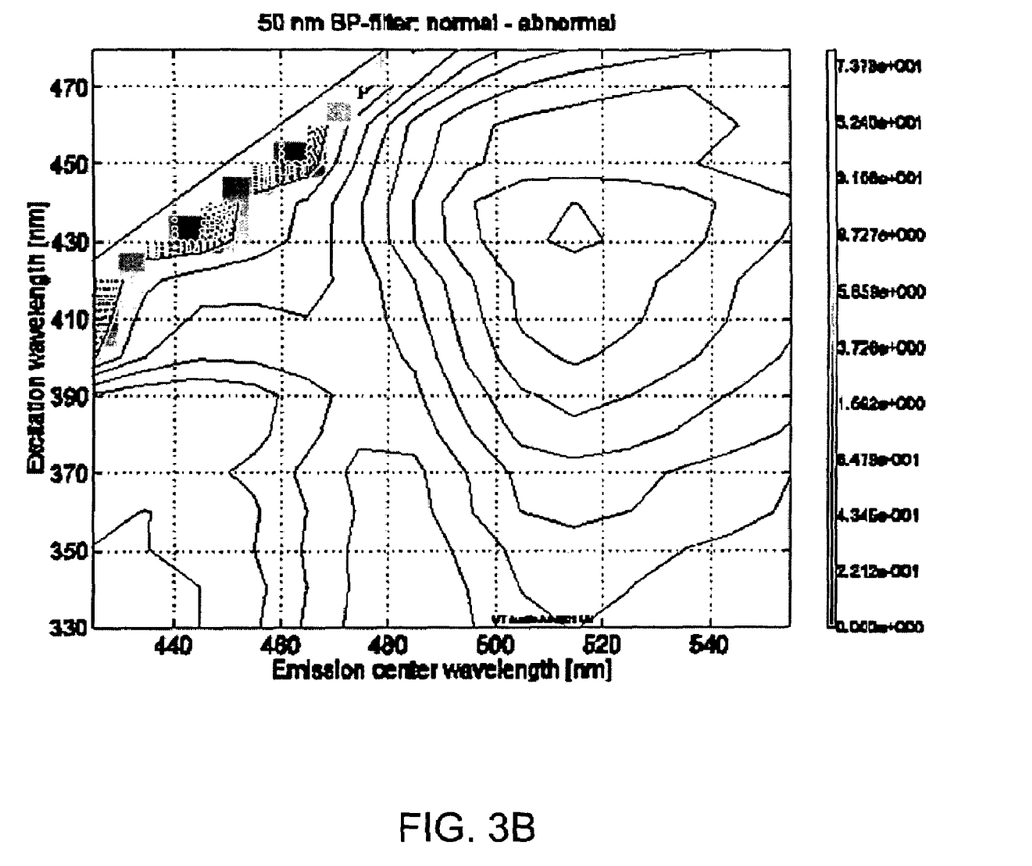
FIG. 3B is an excitation emission matrix of a sample through a bandpass filter with 50 nm bandwidth.
Figure 3C:
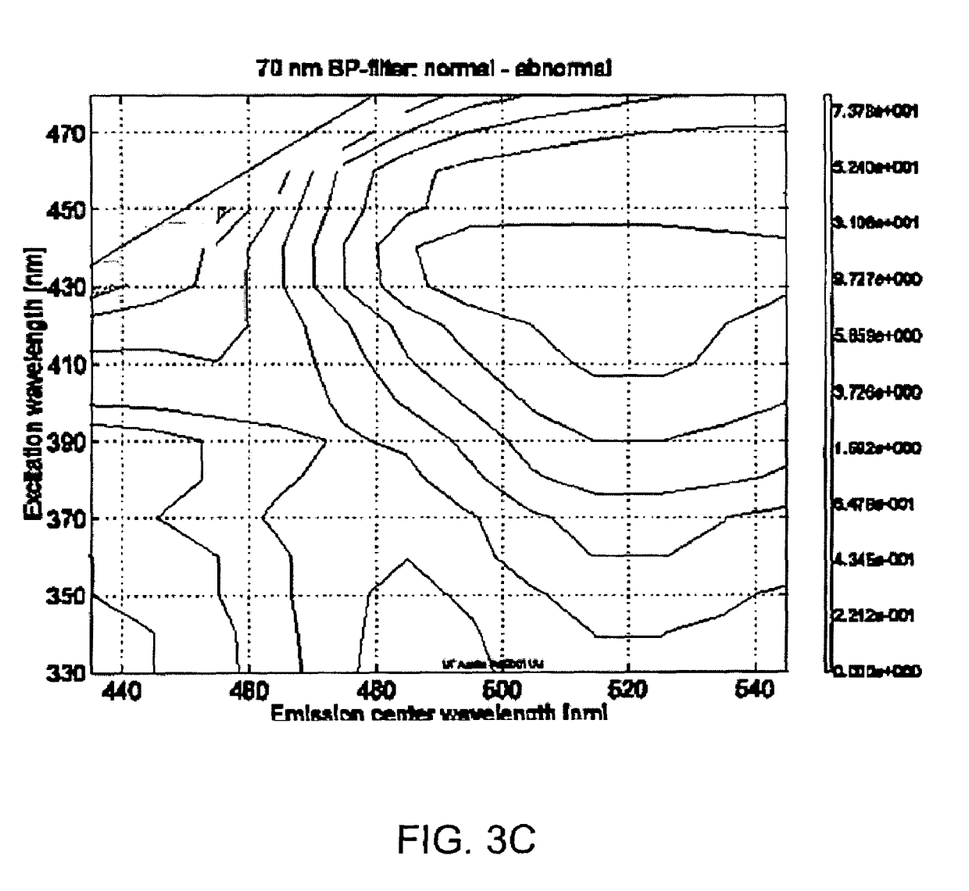
FIG. 3C is an excitation emission matrix of a sample through a bandpass filter with 70 nm bandwidth.

FIGS. 3A to 3C show the result of optimized observation conditions for viewing a sample of oral cavity neoplasia through a bandpass filter; the center wavelength of the observation filter is plotted on the abscissa and the excitation wavelength on the ordinate, and contour lines connect points of equal contrast. In FIG. 3A, the illumination source filter bandpass was set to 20 nm bandwidth, in FIG. 3B to 50 nm, and in FIG. 3C to 70 run. In this embodiment, exciting fluorescence at 430 or 440 nm and observing the emitted light in a band at 510 nm produces the highest contrast in all configurations. Highest contrast is achieved with an illumination source bandpass of 50 nm bandwidth at 430 nm excitation and 51 nm emission. With a 20 nm emission bandpass the maximal contrast is 8% lower than with a 5 nm bandpass and with a 70 nm emission bandpass the contrast is 3% lower. The green range of the visible spectrum is at about 510 nm. At 430/510 nm (excitation/emission wavelength), 410/510 nm, 460/520 nm, 330/430 nm and 380/440 nm areas with a local contrast increase and are observable. When the observation bandpass filter is wider than 50 nm the contrast starts to decrease. The contrast increase through a 50 nm bandpass filter compared to the observation of the full spectral range is approximately 15%.

The system of FIG. 1 may be modified to accommodate other diagnostic tools used in cancer screening. For example, the system may be incorporated into a commercially available tilt-stand colposcope. In one embodiment, the system may include a viewing device which includes a camera mounted on a colposcope. The light source is based on a Xenon arc lamp with an integrated parabolic reflector. The parabolic reflector collects the light from the light bulb and produces a collimated output beam. The fluorescence excitation light is produced using bandpass filters enclosed in a motorized filterwheel which also contains a filter, a cold mirror, that blocks UV light and near infrared light when the device is used in reflectance mode. In one embodiment, a 25 mm focal length UV lens focuses the light onto a 0.25 inch core diameter quartz fiber light guide. The original halogen lamp of the colposcope can be removed to accommodate the fiber optic light guide. A combination of lenses can be attached to the distal end of the probe (illumination optics). This lens combination produces a 3.5 cm diameter illumination spot at a working distance of 30 cm. The measured illumination intensity at this working distance is approximately 0.25 mW/cm2 at 345 nm excitation and 2.4 mW/cm2 at 440 nm excitation.

The colposcope modified as described above may be used to measure white light and fluorescence images of an intact cervix during colposcopy. In one embodiment, the modified colposcope may be used to determine which excitation wavelengths is best for discrimination of the different diagnostic wavelengths and yields the highest diagnostic performance for the full spectrum analysis. Emission spectra with 10 nm and 20 nm bandwidth excitation wavelengths may be used. Data may be measured with 10 nm excitation bandwidth; emission spectra with 20 nm excitation bandwidth and both may be simulated by adding two adjacent emission spectra measured at 10 nm bandwidth excitation.

In order to identify the abnormal areas in the modified colposcope system's fluorescence images, each pixel of a cervical image can be classified to be either squamous neoplasia (SN) or high grade squamous intraepithelial liasons (HGSIL) according to a classification algorithm. The values may be used in a classification algorithm to images from both a 345 nm and a 440 nm excitation. Three ratios can be calculated by dividing each color channel by the sum of the three channels (i.e. R/(R+G+B), G/(R+G+B), B/(R+G+B)) from every pixel of the fluorescence image. As a result, each pixel of the cervical image may be calculated into six corresponding ratios. The simulated data set corresponding to 345 nm and 445 nm excitation used in the diagnostic performance algorithm can be used as a training set for the classification algorithm. Although the training set may be simulated by filtering the full spectral data by the color camera CMY curves, the RGB values outputted by the camera may be used to calculate the ratios for the classification algorithm.

Figure 4:
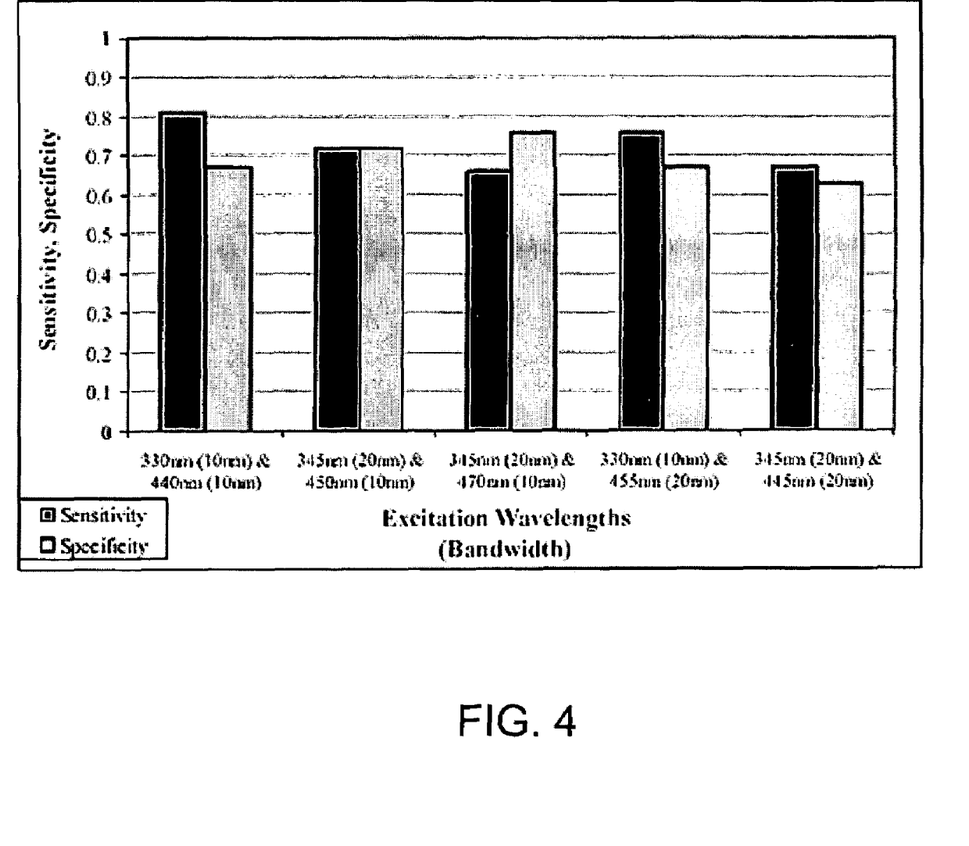
FIG. 4 is a chart comparing excitation bandwidth and wavelength combinations for differentiating squamous neoplasia and high-grade squamous intraepithelial lesions.

FIG. 4 compares the sensitivity and specificity of what the inventors currently consider four best performing excitation wavelength and bandwidth combinations for discrimination between SN and HGSIL, although other combination can be used to and may be found to be even better. The excitation wavelengths are listed in descending order of the sum of the cross-validated sensitivity and specificity. Performance was best with the combination of 335-340 nm and 440-445 nm excitation with a 10 nm bandwidth. However, the autofluorescence of the optical system may be too high at 335 nm excitation wavelength. Excitation at 345 nm gave similar simulated diagnostic performance, while minimizing device autofluorescence. In general, increasing the excitation bandwidth from 10 nm to 20 nm did not significantly change the simulated diagnostic performance. The additional excitation power available with 20 nm bandwidth increased image SNR. Based on these results, the selected excitation wavelengths of 345 nm and 440 nm with 20 nm bandwidth. The expected performance of the MDC under these conditions is also shown in FIG. 4.

With the benefit of the present disclosure, those having skill in the art will comprehend that techniques claimed here and described above may be modified and applied to a number of additional, different applications, achieving the same or a similar result. The claims cover all such modifications that fall within the scope and spirit of this disclosure.

REFERENCES

The following references are incorporated by reference.
American Cancer Society, "Cancer facts & figures—2001", American Cancer Society, Atlanta, Ga., 01-300M-No. 5008.01, 2001.
Andersson-Engels et al., "In vivofluorescence imaging for tissue diagnostics," Phys Med Biol 1997; 42:815-824.
Bergenholtz and Welander, "Ultraviolet autofluorescence: an aid in oral diagnosis," Dent Radiogr Photogr 1970; 43:83-89.
Bernes, R. S., *Billmeyer and Saltzman's principles of color technology*, third edition. New York: John Wiley and Sons Inc., 2000.
Betz et al., "Autofluorescence imaging and spectroscopy of normal and malignant mucosa in patients with head and neck cancer," Lasers Surg Med 1999; 25:323-334.
Blair and Callendar, "Head and neck cancer—the problem", *Clin. Plast. Surg.*, vol. 21, pp. 1-7, 1994.
Boff et al., Handbook of perception and human performance, Vol. 1 Sensory Processes and Perception, John Wiley and Sons.
Brookner et al., "Autofluorescence patterns in short-term cultures of normal cervical tissue.," Photochem Photobiol 2000; 71:730-736.
Commission international de l'eclairage, "Colorimetry 2nd Edition", CIE, Vienna, Austria, CIE 15.2, 1986.
Drezek et al., "Autofluorescence microscopy of fresh cervical-tissue sections reveals alterations in tissue biochemistry with dysplasia.," Photochem Photobiol 2001; 73:636 641.
Geisler, W. S., "Discrimination information in natural radiance spectra," in *Vision models for target detection and recognition*, E. Peli, Ed. Singapore: World Scientific Publishing, 1995.
Geisler, W. S., "Sequential Ideal-Observer Analysis of Visual Discriminations," *Psychological Review*, vol. 96(2), pp. 267-314, 1989.
Georgakoudi et al., "Fluorescence, reflectance, and light scattering spectroscopy for evaluating dysplasia in patients with Barrett's esophagus," Gastroenterology 2001; 120:1620-1629.

Gillenwater et al., "Fluorescence spectroscopy: a technique with potential to improve the early detection of aerodigestive tract neoplasia," Head Neck 1998; 20:556-562. U.S. Department of Health and Human Services, Centers Gillenwater et al., "Noninvasive diagnosis of oral neoplasia based on fluorescence spectroscopy and native tissue autofluorescence," ArchOtolaryngol Head Neck Surgery 1998; 124.

Glasser and Troy, "A new high sensitivity differential calorimeter," *Journal of the Optical Society of America; A*, vol. 42, pp. 652-660, 1952.

Glasser et al., "Cube-root color coordinate system," *Journal of the Optical Society of America; A*, vol. 48, pp. 736-740, 1958.

Guenther and Stiles, "Color Science: Concepts and Methods", Quantitative Data and Formulae, Second Edition, Wiley-Interscience Publication.

Guo et al., "Allelic Losses in OraTest-directed Biopsies of Patients with Prior Upper Aerodigestive Tract Malignancy," Clin. Cancer. Res. vol. 7, pp. 1963-1968, 2001.

Guth et al., "Vector model for normal and dichromatic color vision," *Journal of the Optical Society of America; A*, vol. 70, pp. 197-212, 1980.

Guth, S. L., "Model for color vision and light adaption," *Journal of the Optical Society of America; A*, vol. 8(6), pp. 976-993, 1991.

Harries et al., "Diagnostic imaging of the larynx: autofluorescence of laryngeal tumours using the helium-cadmium laser", *Journal of Laryngology & Otology*, vol. 109(2), pp. 108-10, 1995.

Heintzelman et al., "Optimal Excitation wavelengths for in vivo detection of oral neoplasia using fluorescence spectroscopy," *Photochemistry and Photobiology*, vol. 72, pp. 103-113, 2000.

Jordan et al., "Color as a source of information in the stereo correspondence process," Vision Res. 20 1955-1970.

Jullien et al., "Evaluation of a screening test for the early detection of oral cancer and precancer," Community Dent Health 1995; 12:3-7.

Kaiser and Boynton, "Human Color Vision," Optical Society of America; 1996.

Lakowicz, J. R., "Principles of Fluorescence Spectroscopy," New York: Plenum Press; 1985.

Lakowicz, J R. "Principles of fluorescence spectroscopy," $2^{nd}$ ed., New York: Plenum Publishers; 1999.

MacAdam, D. L., "Visual sensitivities to color differences in daylight," *Journal of the Optical Society of America*, vol. 32, pp. 247-274, 1942.

Mashberg, A., The United States of America as represented by the Department of Health, "Detection of malignant lesions of the oral cavity utilizing toluidine blue rinse", U.S. Pat. No. 4,321,251, 1982.

Mueller et al., "Spectroscopic detection and evaluation of morphologic and biochemical changes in early human oral carcinoma," Cancer 2003; 97:1681-1692.

Palcic et al, "Endoscopic imaging system for diseased tissue" U.S. Pat. No. 5,507,287, 1996.

Onizawa et al.,37 Fluorescence photography as a diagnostic method for oral cancer," Cancer Lett 1996; 108:61-66.

Ramanujam, N., "Fluorescence spectroscopy of neoplastic and non-neoplastic tissues," *Neoplasia*, vol. 2(1-2), pp. 89-117, 2000.

Richards-Kortum et al., "Cervical Dysplasia Diagnosis with Fluorescence Spectroscopy," in *Fluorescence in Biomedicine*, Marcel Dekker, Ed. to be published, 2001.

Richards-Kortum and Sevick-Muraca, "Quantitative Optical Spectroscopy for Tissue Diagnosis," *Annual Reviews in Physical Chemistry*, vol. 47, pp. 555-606, 1996.

Robertson, A. R., "The CIE 1976 color difference formulae," *Color Res. Appl.*, vol. 2, pp. 7-11, 1977.

Schantz et al., "In vivo native cellular fluorescence and histological characteristics of head and neck cancer," Clin Cancer Res 1998; 4:1177-1182.

Sokolov et al., "Realistic Three-Dimensional Epithelial Tissue Phantoms for Biomedical Optics," *Journal of Biomedical Optics*, in press, 2001.

Stockman and Sharpe, "Spectral sensitivities of the middle- and long-wavelength sensitive cones derived from measurements in observers of known genotype," *Vision Research*, vol. 40, pp. 1711-1737, 2000.

Stockman et al., "Spectral sensitivities of the human cones," *Journal of the Optical Society of America; A*, vol. 10(12), pp. 2491-2521, 1993.

Trujillo et al., "A method to determine tissue fluorescence efficiency in vivo and predict signal to noise ratio for spectrometers," *Appl Spectrosc.*, vol. 52, pp. 943-951, 1998.

U.S. Department of Health and Human Services, Centers for Disease Control and Prevention, "Colorectal Cancer: The Importance of Prevention and Early Detection," Atlanta, Ga., 2001.

U.S. Department of Health and Human Services, Centers for Disease Control and Prevention, "Improving Oral Health: Preventing Unnecessary Disease Among All Americans," Atlanta, Ga., 2001.

U.S. Department of Health and Human Services, Centers for Disease Control and Prevention, "The National Breast and Cervical Early Detection Program," Atlanta, Ga., 2001.

Wandell B. Foundation of vision. Sunderland, Mass.: Sinauer Associations; 1995

Wagnieres et al.n, "In vivo fluorescence spectroscopy and imaging for oncological applications," *Photochemistry & Photobiology*, vol. 68(5), pp. 603-32, 1998.

Wandell, B., *Foundation of Vision*. Sunderland, Mass.: Sinauer Associates, 1995.

Wyszecki and Stiles, "The CIE calorimetric system", in *Color science, Concepts and Methods, Quantitative Data and Formulae*, 2nd ed. New York: John Wiley & Sons, 1982.

Wyszecki S. L., "Optical density of the eye, lens, and macular pigment as functions of wavelength", in *Color science, Concepts and Methods, Quantitative Data and Formulae*, 2nd ed. New York: John Wiley & Sons, 1982.

Zuluaga et al., "Fluorescence Excitation Emission Matrices of Human Tissue: A System for in Vivo Measurement and Method of Data Analysis," *Applied Spectroscopy*, vol. 53(3), pp. 302-311, 1999.

The invention claimed is:

1. A system comprising:
   an illumination source;
   a filter coupled to the illumination source that filters radiation from the illumination source to one or more wavelengths between the ranges of about 300 and 625 nanometers;
   a light guide coupled to the filter that directs the one or more wavelengths to a sample; and
   a viewing device in operative relation with the sample that comprises at least one long bandpass filter that filters radiation from the sample to one or more wavelengths between about 320 and 625 nanometers to allow a human eye to directly see the fluorescence reflected from the sample for differentiating between a diseased sample and a normal sample by using the viewing device comprising glasses including observation filters.

2. The system of claim 1, the diseased sample comprising epithelial neoplasia.

3. The system of claim 2, the epithelial neoplasia being selected from the group consisting of skin cancer, cervical cancer, and oral cancer.

4. The system of claim 1, the illumination source comprising a white light source.

5. The system of claim 1, the viewing device comprising a camera coupled to the light guide.

6. The system of claim 5, the camera being attached to a colposcope.

7. The system of claim 1, the filter limiting the radiation from the illumination source to one or more wavelengths between about 400 to 590 nanometers.

8. The system of claim 1, the long bandpass filter filtering radiation from the sample to one or more wavelengths between about 330 and 470 nanometers.

9. The system of claim 8, the long bandpass filter filtering radiation from the sample to one or more wavelengths between about 330 to 360 and about 440 to 470 nanometers to allow a human eye to differentiate between a sample with cervical cancer and a normal sample.

10. The system of claim 8, the long bandpass filter filtering radiation from the sample to one or more wavelengths between about 420 to 470 nanometers to allow a human eye to differentiate between a sample with oral cancer and a normal sample.

11. The system of claim 1, the long bandpass filter having a bandwidth between about 10 to 70 nanometers.

12. The system of claim 1, further comprising a cold mirror coupled to the illumination source that rejects radiation below about 300 nanometers and above about 625 nanometers from the illumination source.

13. The system of claim 1, where a ratio between two or more filtered wavelengths from the illumination source is optimized to increase observable contrast between a diseased sample and a normal sample to a human eye.

14. The system of claim 1, where an attenuation ratio between two or more filtered wavelengths from the sample is optimized to increase observable contrast between a diseased sample and a normal sample to a human eye.

15. A method comprising:
providing a bandpass filter that filters radiation from an illumination source to one or more wavelengths between about 300 to 625 nanometers to illuminate a sample;
filtering radiation from the sample to one or more wavelengths between about 320 to 700 nanometers; and
directly viewing the filtered radiation reflected from the sample with a human eye to differentiate between a diseased sample and a normal sample by using observation filters incorporated into glasses to directly view.

16. The method of claim 15, where providing a bandpass filter further comprises using a cold mirror to reject UV and infrared radiation below about 300 nanometers and above about 625 nanometers.

17. The method of claim 15, the step of providing further comprising coupling the illumination source to a band pass filter that filters radiation from the white light source to one or more wavelengths between about 400 and 590 nanometers.

18. The method of claim 15, the step of providing further comprising using a light guide to direct radiation from the light source to the sample.

19. The method of claim 15, the step of filtering comprising using a long bandpass filter.

20. The method of claim 15, the step of filtering further comprising filtering radiation from the sample to one or more wavelengths between about 330 and 470 nanometers.

21. The method of claim 20, the step of filtering further comprising filtering the radiation from the sample to one or more wavelengths between about 330 to 360 and 440 to 470 nanometers to allow a human eye to differentiate between a sample with cervical cancer and a normal sample.

22. The method of claim 20, the step of filtering further comprising filtering the radiation from the sample to one or more wavelengths between about 420 to 470 nanometers to allow a human eye to differentiate between a sample with oral cancer and a normal sample.

23. The method of claim 15, the step of viewing comprises using a camera for capturing the filtered image.

24. The system of claim 15, where a ratio between two or more filtered wavelengths from the illumination source is optimized to increase observable contrast between a diseased sample and a normal sample to a human eye.

25. The system of claim 15, where an attenuation ratio between two or more filtered wavelengths from the sample is optimized to increase observable contrast between a diseased sample and a normal sample to a human eye.

26. The method of claim 15, the diseased sample comprising epithelial neoplasia selected from the group consisting of oral cancer, skin cancer and cervical cancer.

27. The method of claim 26, the oral cancer being selected from the group consisting of pharynx neoplasia, throat neoplasia, paranasal sinus neoplasia, nasal cavity neoplasia, larynx neoplasia, thyroid neoplasia, parathyroid neoplasia and salivary gland neoplasia.

28. A system comprising:
an illumination source;
a filter coupled to the illumination source that filters radiation from the illumination source to one or more wavelengths between the ranges of about 250 and 700 nanometers;
a light guide coupled to the filter that directs the one or more wavelengths to a sample; and
a viewing device in operative relation with the sample that comprises at least one long bandpass filter that filters radiation from the sample to one or more wavelengths between about 320 and 700 nanometers to allow a human eye to directly see the fluorescence reflected from the sample for differentiating between a diseased sample and a normal sample by using the viewing device comprising glasses including observation filters.

* * * * *